(12) United States Patent
Valaie

(10) Patent No.: US 8,419,748 B2
(45) Date of Patent: Apr. 16, 2013

(54) HELICAL THROMBUS REMOVAL DEVICE

(75) Inventor: Arman H. Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 666 days.

(21) Appl. No.: 11/855,605

(22) Filed: Sep. 14, 2007

(65) Prior Publication Data

US 2009/0076539 A1    Mar. 19, 2009

(51) Int. Cl.
*A61B 17/22* (2006.01)

(52) U.S. Cl.
USPC .......................................................... 606/113

(58) Field of Classification Search ............... 606/113, 606/114, 200, 127; 623/1.22
See application file for complete search history.

(56) References Cited

U.S. PATENT DOCUMENTS

| | | | |
|---|---|---|---|
| 3,108,593 A | 10/1963 | Glassman | |
| 3,334,629 A | 8/1967 | Cohn | |
| 3,472,230 A | 10/1969 | Fogarty | |
| 3,547,103 A | 12/1970 | Cook | |
| 3,635,223 A | 1/1972 | Klieman | |
| 3,923,065 A | 12/1975 | Nozick et al. | |
| 3,952,747 A | 4/1976 | Kimmell, Jr. | |
| 3,978,863 A | 9/1976 | Fettel et al. | |
| 3,996,938 A | 12/1976 | Clark, III | |
| 4,425,908 A | 1/1984 | Simon | |
| 4,456,000 A | 6/1984 | Schjeldahl et al. | |
| 4,494,531 A | 1/1985 | Gianturco | |
| 4,548,206 A | 10/1985 | Osborne | |
| 4,561,439 A | 12/1985 | Bishop et al. | |
| 4,562,039 A | 12/1985 | Koehler | |
| 4,604,094 A | 8/1986 | Shook | |
| 4,619,246 A | 10/1986 | Molgaard-Nielsen et al. | |
| 4,643,184 A | 2/1987 | Mobin-Uddin | |
| 4,646,736 A | 3/1987 | Auth | |

(Continued)

FOREIGN PATENT DOCUMENTS

| | | |
|---|---|---|
| DE | 3429850 A1 | 2/1986 |
| EP | 1127556 A2 | 8/2001 |

(Continued)

OTHER PUBLICATIONS

Rubicon Embolic Filter, The Next Generation of EM, Rubicon Medical, www.rubiconmed.com.

(Continued)

*Primary Examiner* — Ryan Severson
(74) *Attorney, Agent, or Firm* — Brinks Hofer Gilson & Lione

(57) ABSTRACT

A device for removing thrombus from a body cavity is disclosed. The device comprises a flexible wire having a proximal end and a distal end. The device further comprises an elongated shaft having a proximal portion and a distal portion. The proximal portion attached to the distal end of the flexible wire and distally extends therefrom to the distal portion. The device further comprises an expandable member formed helically about the elongated shaft. The expandable member is configured to helically close, defining a collapsed state for delivery and retrieval of the device. The expandable member is configured to helically open, defining an expanded state for removing thrombus from the body cavity. The expandable member has at least one member portion helically extending from the elongated shaft at a predetermined angle, defining a proximally faced opening when the member is in the expanded state.

20 Claims, 5 Drawing Sheets

U.S. PATENT DOCUMENTS

| | | | |
|---|---|---|---|
| 4,650,472 A | 3/1987 | Bates | |
| 4,665,906 A | 5/1987 | Jervis | |
| 4,669,464 A | 6/1987 | Sulepov | |
| 4,688,553 A | 8/1987 | Metals | |
| 4,723,549 A | 2/1988 | Wholey et al. | |
| 4,727,873 A | 3/1988 | Mobin-Uddin | |
| 4,732,152 A | 3/1988 | Wallsten et al. | |
| 4,817,600 A | 4/1989 | Herms et al. | |
| 4,824,435 A | 4/1989 | Giesy et al. | |
| 4,832,055 A | 5/1989 | Palestrant | |
| 4,848,343 A | 7/1989 | Wallsten et al. | |
| 4,873,978 A | 10/1989 | Ginsburg | |
| 4,943,297 A | 7/1990 | Saveliev et al. | |
| 4,957,501 A | 9/1990 | Lahille et al. | |
| 4,990,156 A | 2/1991 | Lefebvre | |
| 4,998,916 A | 3/1991 | Hammerslag et al. | |
| 5,053,008 A | 10/1991 | Bajaj | |
| 5,059,205 A | 10/1991 | El-Nounou et al. | |
| 5,069,226 A | 12/1991 | Yamauchi et al. | |
| 5,078,726 A | 1/1992 | Kreamer | |
| 5,100,423 A | 3/1992 | Fearnot | |
| 5,108,418 A | 4/1992 | Lefebvre | |
| 5,108,419 A | 4/1992 | Reger et al. | |
| 5,112,347 A | 5/1992 | Taheri | |
| 5,129,890 A | 7/1992 | Bates et al. | |
| 5,133,733 A | 7/1992 | Rasmussen et al. | |
| 5,147,379 A | 9/1992 | Sabbaghian et al. | |
| 5,152,777 A | 10/1992 | Goldberg | |
| 5,160,342 A * | 11/1992 | Reger et al. | 606/200 |
| 5,163,927 A | 11/1992 | Woker et al. | |
| 5,203,772 A | 4/1993 | Hammerslag et al. | |
| 5,234,458 A | 8/1993 | Metais | |
| 5,242,462 A | 9/1993 | El-Nounou | |
| 5,243,996 A | 9/1993 | Hall | |
| 5,251,640 A | 10/1993 | Osborne | |
| 5,263,964 A | 11/1993 | Purdy | |
| 5,300,086 A | 4/1994 | Gory et al. | |
| 5,324,304 A | 6/1994 | Rasmussen | |
| 5,329,942 A | 7/1994 | Gunther et al. | |
| 5,344,427 A | 9/1994 | Cottenceau et al. | |
| 5,350,397 A | 9/1994 | Palermo et al. | |
| 5,350,398 A | 9/1994 | Pavcnik et al. | |
| 5,364,345 A | 11/1994 | Lowery et al. | |
| 5,370,657 A | 12/1994 | Irie | |
| 5,375,612 A | 12/1994 | Cottenceau et al. | |
| 5,383,887 A | 1/1995 | Nadal | |
| 5,413,586 A | 5/1995 | Dibie et al. | |
| 5,415,630 A | 5/1995 | Gory et al. | |
| 5,417,708 A | 5/1995 | Hall et al. | |
| 5,451,233 A | 9/1995 | Yock | |
| 5,458,573 A | 10/1995 | Summers | |
| 5,522,881 A | 6/1996 | Lentz | |
| 5,527,338 A | 6/1996 | Purdy | |
| 5,531,788 A | 7/1996 | Dibie et al. | |
| 5,549,551 A | 8/1996 | Peacock et al. | |
| 5,549,626 A | 8/1996 | Miller et al. | |
| 5,556,414 A | 9/1996 | Turi | |
| 5,562,698 A | 10/1996 | Parker | |
| 5,591,195 A | 1/1997 | Taheri et al. | |
| 5,601,595 A | 2/1997 | Smith | |
| 5,624,461 A | 4/1997 | Mariant | |
| 5,626,605 A | 5/1997 | Irie et al. | |
| 5,630,797 A | 5/1997 | Diedrich et al. | |
| 5,634,942 A | 6/1997 | Chevillon et al. | |
| 5,649,953 A | 7/1997 | Lefebvre | |
| 5,662,703 A | 9/1997 | Yurek et al. | |
| 5,669,933 A | 9/1997 | Simon et al. | |
| 5,681,347 A | 10/1997 | Cathcart et al. | |
| 5,690,642 A | 11/1997 | Osborne et al. | |
| 5,690,667 A | 11/1997 | Gia | |
| 5,693,067 A | 12/1997 | Purdy | |
| 5,693,087 A | 12/1997 | Parodi | |
| 5,695,518 A | 12/1997 | Laerum | |
| 5,695,519 A | 12/1997 | Summers et al. | |
| 5,700,253 A | 12/1997 | Parker | |
| 5,709,704 A | 1/1998 | Nott et al. | |
| 5,713,853 A | 2/1998 | Clark et al. | |
| 5,720,764 A | 2/1998 | Naderlinger | |
| 5,725,550 A | 3/1998 | Nadal | |
| 5,738,667 A | 4/1998 | Solar | |
| 5,746,767 A | 5/1998 | Smith | |
| 5,755,772 A | 5/1998 | Evans et al. | |
| 5,755,790 A | 5/1998 | Chevillon et al. | |
| 5,766,203 A | 6/1998 | Imran et al. | |
| 5,769,816 A | 6/1998 | Barbut et al. | |
| 5,769,871 A | 6/1998 | Mers et al. | |
| 5,795,322 A | 8/1998 | Boudewijn | |
| 5,800,457 A | 9/1998 | Gelbfish et al. | |
| 5,800,525 A | 9/1998 | Bachinski et al. | |
| 5,810,874 A | 9/1998 | Lefebvre | |
| 5,814,027 A | 9/1998 | Hassett et al. | |
| 5,814,064 A | 9/1998 | Daniel et al. | |
| 5,820,592 A | 10/1998 | Hammerslag | |
| 5,827,324 A | 10/1998 | Cassell et al. | |
| 5,830,230 A | 11/1998 | Berryman et al. | |
| 5,836,968 A | 11/1998 | Simon et al. | |
| 5,836,969 A | 11/1998 | Kim et al. | |
| 5,846,260 A | 12/1998 | Maahs | |
| 5,853,420 A | 12/1998 | Chevillon et al. | |
| 5,876,367 A | 3/1999 | Kaganov et al. | |
| 5,893,869 A | 4/1999 | Barnhart et al. | |
| 5,895,391 A | 4/1999 | Farnholtz | |
| 5,895,399 A | 4/1999 | Barbut et al. | |
| 5,895,410 A | 4/1999 | Forber et al. | |
| 5,908,435 A | 6/1999 | Samuels | |
| 5,910,154 A | 6/1999 | Tsugita et al. | |
| 5,911,702 A | 6/1999 | Romley et al. | |
| 5,911,704 A | 6/1999 | Humes | |
| 5,911,717 A | 6/1999 | Jacobsen et al. | |
| 5,911,734 A | 6/1999 | Tsugita et al. | |
| 5,919,224 A | 7/1999 | Thompson et al. | |
| 5,925,062 A | 7/1999 | Purdy | |
| 5,925,063 A | 7/1999 | Khosravi | |
| 5,928,260 A | 7/1999 | Chine et al. | |
| 5,928,261 A | 7/1999 | Ruiz | |
| 5,938,683 A | 8/1999 | Lefebvre | |
| 5,941,896 A | 8/1999 | Kerr | |
| 5,944,728 A | 8/1999 | Bates | |
| 5,947,985 A | 9/1999 | Imran | |
| 5,947,995 A | 9/1999 | Samuels | |
| 5,948,017 A | 9/1999 | Taheri | |
| 5,951,567 A | 9/1999 | Javier, Jr. et al. | |
| 5,954,741 A | 9/1999 | Fox | |
| 5,954,742 A | 9/1999 | Osypka | |
| 5,954,745 A | 9/1999 | Gertler et al. | |
| 5,968,057 A | 10/1999 | Taheri | |
| 5,968,071 A | 10/1999 | Chevillon et al. | |
| 5,972,019 A | 10/1999 | Engelson et al. | |
| 5,976,162 A | 11/1999 | Doan et al. | |
| 5,976,172 A | 11/1999 | Homsma et al. | |
| 5,980,555 A | 11/1999 | Barbut et al. | |
| 5,984,947 A | 11/1999 | Smith | |
| 5,984,965 A | 11/1999 | Knapp et al. | |
| 5,989,281 A | 11/1999 | Barbut et al. | |
| 6,001,118 A | 12/1999 | Daniel et al. | |
| 6,007,557 A | 12/1999 | Ambrisco et al. | |
| 6,007,558 A | 12/1999 | Ravenscloth et al. | |
| 6,010,522 A | 1/2000 | Barbut et al. | |
| 6,013,093 A | 1/2000 | Nott et al. | |
| 6,015,424 A | 1/2000 | Rosenbluth et al. | |
| 6,027,520 A | 2/2000 | Tsugita et al. | |
| 6,036,717 A | 3/2000 | Mers et al. | |
| 6,036,720 A | 3/2000 | Abrams et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,745 A | 5/2000 | Gelbfish | |
| 6,059,813 A | 5/2000 | Vrba et al. | |
| 6,059,814 A | 5/2000 | Ladd | |
| 6,063,113 A | 5/2000 | Kavteladze et al. | |
| 6,066,158 A | 5/2000 | Engelson et al. | |
| 6,068,645 A | 5/2000 | Tu | |
| 6,074,357 A | 6/2000 | Kaganov et al. | |
| 6,077,274 A | 6/2000 | Ouchi et al. | |
| 6,080,178 A | 6/2000 | Meglin | |
| 6,083,239 A | 7/2000 | Addis | |

| Patent | Type | Date | Inventor |
|---|---|---|---|
| 6,086,577 | A | 7/2000 | Ken et al. |
| 6,086,605 | A | 7/2000 | Barbut et al. |
| 6,093,199 | A | 7/2000 | Brown et al. |
| 6,096,053 | A | 8/2000 | Bates |
| 6,096,070 | A | 8/2000 | Ragheb et al. |
| 6,099,549 | A | 8/2000 | Bosma et al. |
| 6,106,497 | A | 8/2000 | Wang |
| 6,126,672 | A | 10/2000 | Berryman et al. |
| 6,126,673 | A | 10/2000 | Kim et al. |
| 6,129,739 | A | 10/2000 | Khosravi |
| 6,136,016 | A | 10/2000 | Barbut et al. |
| 6,146,396 | A | 11/2000 | Konya et al. |
| 6,146,404 | A | 11/2000 | Kim et al. |
| 6,152,931 | A | 11/2000 | Nadal et al. |
| 6,152,946 | A | 11/2000 | Broome et al. |
| 6,152,947 | A | 11/2000 | Ambrisco et al. |
| 6,156,061 | A | 12/2000 | Wallace et al. |
| 6,156,062 | A | 12/2000 | McGuinness |
| 6,159,230 | A | 12/2000 | Samuels |
| 6,165,179 | A | 12/2000 | Cathcart et al. |
| 6,165,198 | A | 12/2000 | McGurk et al. |
| 6,165,199 | A | 12/2000 | Barbut |
| 6,165,200 | A * | 12/2000 | Tsugita et al. ............... 606/200 |
| 6,168,579 | B1 | 1/2001 | Tsugita et al. |
| 6,168,603 | B1 | 1/2001 | Leslie et al. |
| 6,168,610 | B1 | 1/2001 | Marin et al. |
| 6,168,622 | B1 | 1/2001 | Mazzocchi |
| 6,171,327 | B1 | 1/2001 | Daniel et al. |
| 6,171,328 | B1 | 1/2001 | Addis |
| 6,174,318 | B1 | 1/2001 | Bates et al. |
| 6,179,851 | B1 | 1/2001 | Barbut et al. |
| 6,179,859 | B1 | 1/2001 | Bates et al. |
| 6,179,860 | B1 | 1/2001 | Fulton, III et al. |
| 6,179,861 | B1 | 1/2001 | Khosravi et al. |
| 6,187,025 | B1 | 2/2001 | Machek |
| 6,193,739 | B1 | 2/2001 | Chevillon et al. |
| 6,203,561 | B1 | 3/2001 | Ramee et al. |
| 6,206,931 | B1 | 3/2001 | Cook et al. |
| 6,214,025 | B1 | 4/2001 | Thistle et al. |
| 6,214,026 | B1 | 4/2001 | Lepak et al. |
| 6,221,091 | B1 | 4/2001 | Khosravi |
| 6,224,620 | B1 | 5/2001 | Maahs |
| 6,231,588 | B1 | 5/2001 | Zadno-Azizi |
| 6,231,589 | B1 | 5/2001 | Wessman et al. |
| 6,235,044 | B1 | 5/2001 | Root et al. |
| 6,235,045 | B1 | 5/2001 | Barbut et al. |
| 6,238,412 | B1 | 5/2001 | Dubrul et al. |
| 6,241,746 | B1 | 6/2001 | Bosma et al. |
| 6,245,087 | B1 | 6/2001 | Addis |
| 6,245,088 | B1 | 6/2001 | Lowery |
| 6,245,089 | B1 | 6/2001 | Daniel et al. |
| 6,251,092 | B1 | 6/2001 | Qin et al. |
| 6,251,122 | B1 | 6/2001 | Tsukernik |
| 6,254,550 | B1 | 7/2001 | McNamara et al. |
| 6,254,633 | B1 | 7/2001 | Pinchuk et al. |
| 6,258,026 | B1 | 7/2001 | Ravenscroft et al. |
| 6,258,115 | B1 | 7/2001 | Dubrul |
| 6,258,120 | B1 | 7/2001 | McKenzie et al. |
| 6,261,305 | B1 | 7/2001 | Marotta et al. |
| 6,264,672 | B1 | 7/2001 | Fisher |
| 6,267,776 | B1 | 7/2001 | O'Connell |
| 6,267,777 | B1 | 7/2001 | Bosma et al. |
| 6,273,900 | B1 | 8/2001 | Nott et al. |
| 6,273,901 | B1 | 8/2001 | Whitcher et al. |
| 6,277,125 | B1 | 8/2001 | Barry et al. |
| 6,277,126 | B1 | 8/2001 | Barry et al. |
| 6,277,138 | B1 | 8/2001 | Levinson et al. |
| 6,277,139 | B1 | 8/2001 | Levinson et al. |
| 6,280,451 | B1 | 8/2001 | Bates et al. |
| 6,287,321 | B1 | 9/2001 | Jang |
| 6,290,710 | B1 | 9/2001 | Cryer et al. |
| 6,299,604 | B1 | 10/2001 | Ragheb et al. |
| 6,306,163 | B1 | 10/2001 | Fitz |
| 6,309,399 | B1 | 10/2001 | Barbut et al. |
| 6,312,444 | B1 | 11/2001 | Barbut |
| 6,319,268 | B1 | 11/2001 | Ambrisco et al. |
| 6,325,815 | B1 | 12/2001 | Kusleika et al. |
| 6,325,816 | B1 | 12/2001 | Fulton, III et al. |
| 6,328,755 | B1 | 12/2001 | Marshall |
| 6,331,183 | B1 | 12/2001 | Suon |
| 6,331,184 | B1 | 12/2001 | Abrams |
| 6,334,864 | B1 | 1/2002 | Amplatz et al. |
| 6,336,934 | B1 | 1/2002 | Gilson et al. |
| 6,338,739 | B1 | 1/2002 | Datta et al. |
| 6,340,364 | B2 | 1/2002 | Kanesaka |
| 6,342,062 | B1 | 1/2002 | Suon et al. |
| 6,342,063 | B1 | 1/2002 | DeVries et al. |
| 6,344,048 | B1 | 2/2002 | Chin et al. |
| 6,344,049 | B1 | 2/2002 | Levinson et al. |
| 6,346,116 | B1 | 2/2002 | Brooks et al. |
| 6,348,041 | B1 | 2/2002 | Klint |
| 6,348,063 | B1 | 2/2002 | Yassour et al. |
| 6,355,051 | B1 | 3/2002 | Sisskind et al. |
| 6,358,228 | B1 | 3/2002 | Tubman et al. |
| 6,361,545 | B1 | 3/2002 | Macoviak et al. |
| 6,361,546 | B1 | 3/2002 | Khosravi |
| 6,361,547 | B1 | 3/2002 | Hieshima |
| 6,364,895 | B1 | 4/2002 | Greenhalgh |
| 6,364,896 | B1 | 4/2002 | Addis |
| 6,368,338 | B1 | 4/2002 | Konya et al. |
| 6,371,961 | B1 | 4/2002 | Osborne et al. |
| 6,371,969 | B1 | 4/2002 | Tsugita et al. |
| 6,371,970 | B1 | 4/2002 | Khosravi et al. |
| 6,371,971 | B1 | 4/2002 | Tsugita et al. |
| 6,375,670 | B1 | 4/2002 | Greenhalgh |
| 6,379,374 | B1 | 4/2002 | Hieshima et al. |
| 6,380,457 | B1 | 4/2002 | Yurek et al. |
| 6,383,146 | B1 | 5/2002 | Klint |
| 6,383,171 | B1 | 5/2002 | Gifford et al. |
| 6,383,174 | B1 | 5/2002 | Eder |
| 6,383,193 | B1 | 5/2002 | Cathcart et al. |
| 6,383,196 | B1 | 5/2002 | Leslie et al. |
| 6,383,205 | B1 | 5/2002 | Samson et al. |
| 6,383,206 | B1 | 5/2002 | Gillick et al. |
| 6,391,044 | B1 | 5/2002 | Yadav et al. |
| 6,391,045 | B1 | 5/2002 | Kim et al. |
| 6,391,052 | B2 | 5/2002 | Buirge et al. |
| 6,395,014 | B1 | 5/2002 | Macoviak et al. |
| 6,402,771 | B1 | 6/2002 | Palmer et al. |
| 6,402,772 | B1 | 6/2002 | Amplatz et al. |
| 6,409,742 | B1 | 6/2002 | Fulton, III et al. |
| 6,413,235 | B1 | 7/2002 | Parodi |
| 6,416,530 | B2 | 7/2002 | DeVries et al. |
| 6,419,686 | B1 | 7/2002 | McLeod et al. |
| 6,423,052 | B1 | 7/2002 | Escano |
| 6,423,086 | B1 | 7/2002 | Barbut et al. |
| 6,425,909 | B1 | 7/2002 | Dieck et al. |
| 6,428,557 | B1 | 8/2002 | Hilaire |
| 6,428,558 | B1 | 8/2002 | Jones et al. |
| 6,428,559 | B1 | 8/2002 | Johnson |
| 6,432,122 | B1 | 8/2002 | Gilson et al. |
| 6,436,112 | B2 | 8/2002 | Wensel et al. |
| 6,436,120 | B1 | 8/2002 | Meglin |
| 6,436,121 | B1 | 8/2002 | Blom |
| 6,443,926 | B1 | 9/2002 | Kletschka |
| 6,443,971 | B1 | 9/2002 | Boylan et al. |
| 6,443,972 | B1 | 9/2002 | Bosma et al. |
| 6,447,530 | B1 | 9/2002 | Ostrovsky et al. |
| 6,447,531 | B1 | 9/2002 | Amplatz |
| 6,454,775 | B1 | 9/2002 | Demarais et al. |
| 6,458,139 | B1 | 10/2002 | Palmer et al. |
| 6,458,145 | B1 | 10/2002 | Ravenscroft et al. |
| 6,461,370 | B1 | 10/2002 | Gray et al. |
| 6,468,290 | B1 | 10/2002 | Weldon et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,500 | B1 | 11/2002 | Kokish et al. |
| 6,485,501 | B1 | 11/2002 | Green |
| 6,485,502 | B2 | 11/2002 | Don Michael et al. |
| 6,491,712 | B1 | 12/2002 | O'Connor |
| 6,494,895 | B2 | 12/2002 | Addis |
| 6,497,709 | B1 | 12/2002 | Heath |
| 6,499,487 | B1 | 12/2002 | McKenzie et al. |
| 6,500,166 | B1 | 12/2002 | Zadno Azizi et al. |
| 6,500,191 | B2 | 12/2002 | Addis |
| 6,502,606 | B2 | 1/2003 | Klint |
| 6,506,203 | B1 | 1/2003 | Boyle et al. |

| Patent No. | Date | Inventor(s) |
|---|---|---|
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 | 2/2004 | Boyle et al. |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,855 B2 | 6/2004 | Yurek et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,866,677 B2 | 3/2005 | Douk et al. |
| 6,866,680 B2 | 3/2005 | Yassour et al. |
| 6,896,691 B2 | 5/2005 | Boylan et al. |
| 6,929,709 B2 | 8/2005 | Smith |
| 6,932,831 B2 | 8/2005 | Forber |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,097,651 B2 | 8/2006 | Harrison et al. |
| 7,128,073 B1 | 10/2006 | Van Der Burg et al. |
| 7,189,249 B2 | 3/2007 | Hart et al. |
| 7,255,687 B2 | 8/2007 | Huang et al. |
| 7,285,130 B2 | 10/2007 | Austin |
| 7,306,619 B1 | 12/2007 | Palmer |
| 7,371,248 B2 | 5/2008 | Dapolito et al. |
| 7,393,358 B2 | 7/2008 | Malewicz |
| 7,766,934 B2 | 8/2010 | Pal et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |

| | | |
|---|---|---|
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1 | 7/2002 | Becker et al. |
| 2002/0099435 A1 | 7/2002 | Stinson |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1 | 11/2002 | Eum et al. |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004537 A1 | 1/2003 | Boyle et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucek |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Don Michael |
| 2003/0055452 A1 | 3/2003 | Joergensen et al. |
| 2003/0055480 A1 | 3/2003 | Fischell et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0065355 A1 | 4/2003 | Weber |
| 2003/0065356 A1 | 4/2003 | Tsugita et al. |
| 2003/0069596 A1 | 4/2003 | Eskuri |
| 2003/0073979 A1 | 4/2003 | Naimark et al. |
| 2003/0074019 A1 | 4/2003 | Gray et al. |
| 2003/0078614 A1 | 4/2003 | Salahieh et al. |
| 2003/0083608 A1 | 5/2003 | Evans et al. |
| 2003/0083692 A1 | 5/2003 | Vrba et al. |
| 2003/0083693 A1 | 5/2003 | Daniel et al. |
| 2003/0088211 A1 | 5/2003 | Anderson et al. |
| 2003/0088266 A1 | 5/2003 | Bowlin |

| Publication No. | Date | Inventor |
|---|---|---|
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0109916 A1 | 6/2003 | Don Michael |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171800 A1 | 9/2003 | Bicek et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212431 A1 | 11/2003 | Brady et al. |
| 2003/0212432 A1 | 11/2003 | Khairkhahan et al. |
| 2003/0212433 A1 | 11/2003 | Ambrisco et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225418 A1 | 12/2003 | Esksuri et al. |
| 2003/0225435 A1 | 12/2003 | Hunter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006370 A1 | 1/2004 | Tsugita |
| 2004/0015152 A1 | 1/2004 | Day |
| 2004/0039412 A1 | 2/2004 | Isshiki et al. |
| 2004/0049226 A1 | 3/2004 | Keegan et al. |
| 2004/0054394 A1 | 3/2004 | Lee |
| 2004/0054395 A1 | 3/2004 | Lee et al. |
| 2004/0059372 A1 | 3/2004 | Tsugita |
| 2004/0064067 A1 | 4/2004 | Ward |
| 2004/0064179 A1 | 4/2004 | Linder et al. |
| 2004/0068271 A1 | 4/2004 | McAlister |
| 2004/0078044 A1 | 4/2004 | Kear |
| 2004/0082962 A1 | 4/2004 | Demarais et al. |
| 2004/0088038 A1 | 5/2004 | Dehnad et al. |
| 2004/0093009 A1 | 5/2004 | Denison et al. |
| 2004/0093012 A1 | 5/2004 | Cully et al. |
| 2004/0093016 A1 | 5/2004 | Root et al. |
| 2004/0093059 A1 | 5/2004 | Lee et al. |
| 2004/0098022 A1 | 5/2004 | Barone |
| 2004/0098026 A1 | 5/2004 | Joergensen et al. |
| 2004/0098033 A1 | 5/2004 | Leeflang et al. |
| 2004/0098112 A1 | 5/2004 | DiMatteo et al. |
| 2004/0102719 A1 | 5/2004 | Keith et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0138696 A1 | 7/2004 | Drasler et al. |
| 2004/0153118 A1 | 8/2004 | Clubb et al. |
| 2004/0158278 A1 | 8/2004 | Becker et al. |
| 2004/0162576 A1 | 8/2004 | Barbut et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0027345 A1 | 2/2005 | Horan et al. |
| 2005/0038468 A1 | 2/2005 | Panetta et al. |
| 2005/0038503 A1 | 2/2005 | Greenhalgh |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009798 A1 | 1/2006 | Callister et al. |
| 2006/0009799 A1 | 1/2006 | Kleshinski et al. |

| | | |
|---|---|---|
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287667 A1 * | 12/2006 | Abela ............ 606/200 |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0167974 A1 | 7/2007 | Cully et al. |
| 2007/0185521 A1 | 8/2007 | Bui et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |

OTHER PUBLICATIONS

Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," Modelling in Medicine and Biology IV, (2005), vol. 8, pp. 133.

* cited by examiner

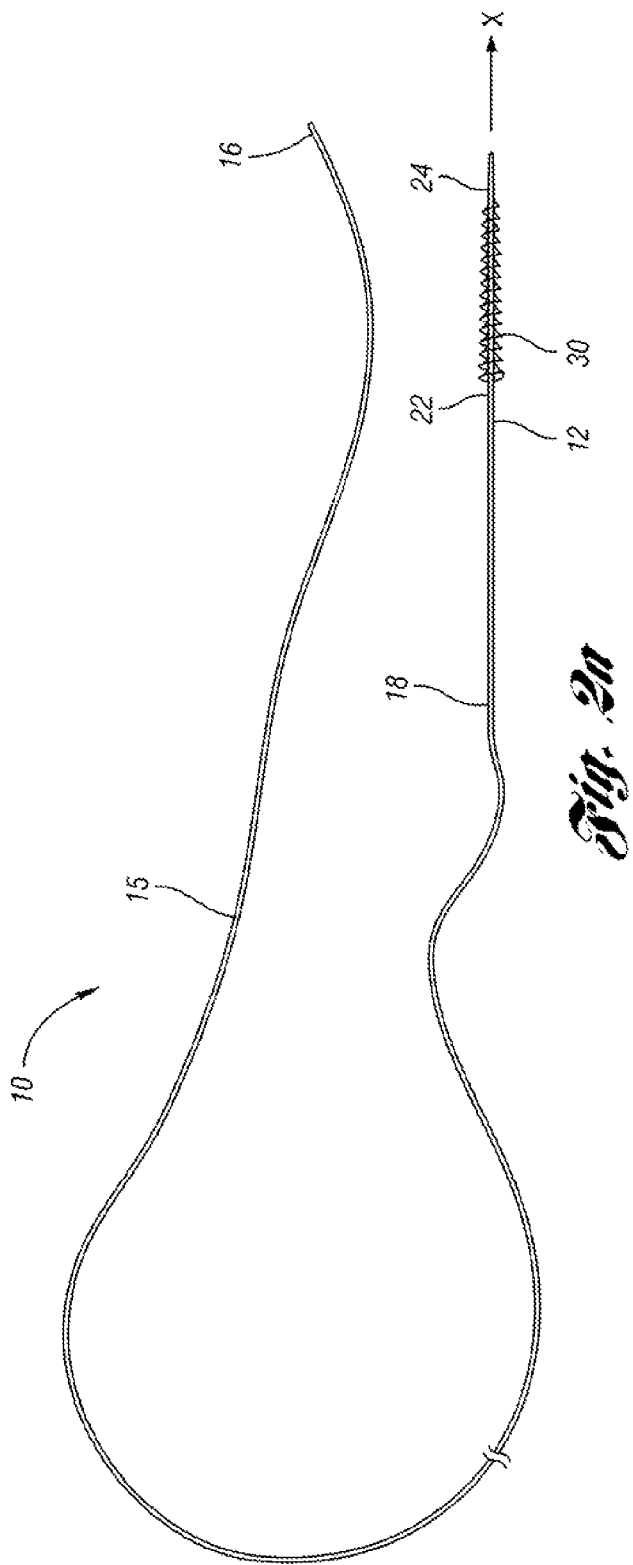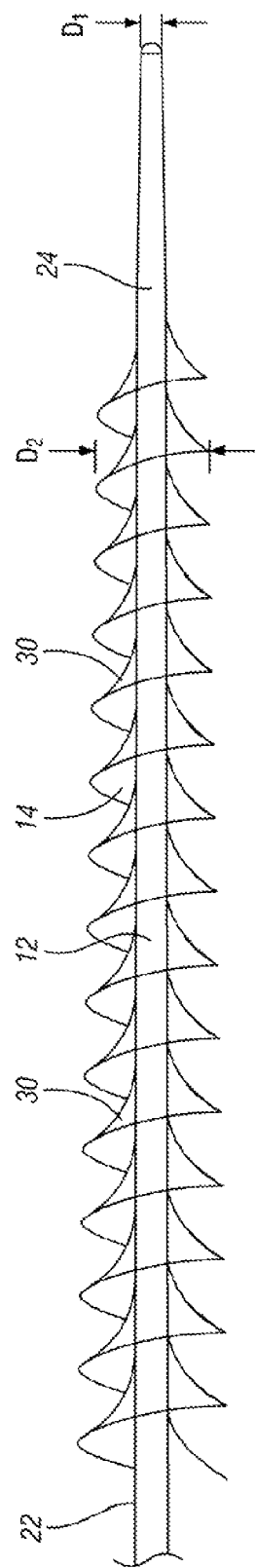

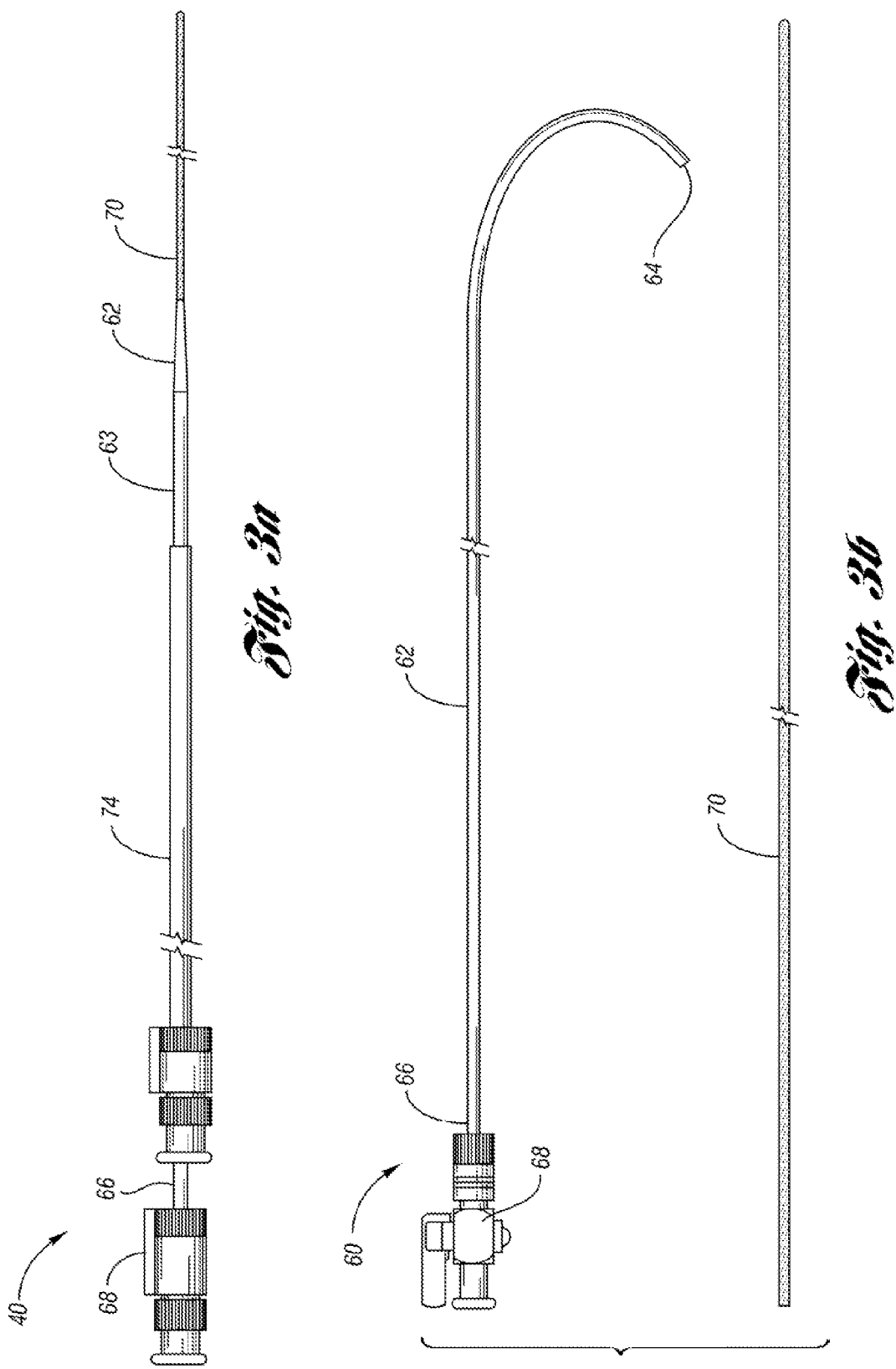

HELICAL THROMBUS REMOVAL DEVICE

BACKGROUND OF THE INVENTION

The present invention relates to medical devices. Specifically, the invention relates to a device for removing blood clots or thrombi from body vessels, such as the small arteries associated with the brain.

Mechanical thrombectomy is a procedure that has been in widespread use for many years. Typical thrombectomy devices are balloons that are inflated in a vessel and then withdrawn to pull clots into a sheath which can be withdrawn from the patient to remove the clots. Other devices are simple open ended catheters into which a clot is aspirated and removed from the patient. Another thrombectomy device employs a basket device that is opened within the clot so that the clot becomes captured in the basket. The basket can then be retrieved along with the clot. Still other devices use a small corkscrew shaped device that is collapsed inside a catheter. The catheter is passed through the clot, the corkscrew is pushed out of the catheter allowing the device to expand, capturing the clot for removal. Some corkscrew devices are simply "screwed" into the clot, then retracted into a catheter for removal before the corkscrew is retracted.

Although adequate, many of these devices have certain disadvantages. For example, the balloon catheter devices are first advanced through the clot before they can be inflated and retracted. The process of penetrating the clot with the balloon catheter device tends to push the clot deeper into the arterial circulation where it becomes even more difficult to remove. This issue also occurs with basket and corkscrew devices that are collapsed into an outer delivery sheath and passed through the clot before they can be deployed and retracted. The action of pushing a device through the center of the clot pushes the clot deeper into the artery and sometimes fragments the clot, making it into an even more dangerous embolus. The corkscrew devices that are screwed into the clot usually have a smooth rounded tip to prevent the corkscrew from penetrating the vessel wall or otherwise damaging the vessel wall as it is screwed into the clot. With these devices, however, the smooth, rounded central tip does not screw into the clot, but instead is pushed into the clot and then the remainder of the corkscrew is screwed into the clot. This results in a pushing force on the center of the clot and a pulling force on the periphery of the clot. These counter forces tend to macerate or fragment the clot and result in only a small part of the clot being captured. Some corkscrew devices may substitute a sharp tip that can screw directly into the clot for the rounded tip. However, sharp tips can penetrate the vessel wall just as easily as they can penetrate and capture the clot. Such devices are seldom used since they carry the very high risk of penetrating the vessel wall. When a bead or ball is applied to the tip of the device that is large enough to protect the vessel wall, it will be so large that it will tend to push the clot distally rather than penetrate the clot such that the clot can be captured and removed.

Another issue associated with conventional thrombectomy devices is that they have relatively large cross-sectional profiles and, in turn, are relatively too stiff for use in the small tortuous vessels of the brain. In view of the above, it is apparent that there exists a need for an improved mechanical thrombectomy device.

BRIEF SUMMARY OF THE INVENTION

The present invention generally provides a clot removal device that has a reduced cross-sectional profile and an improved flexibility to allow for treatment in smaller tortuous body vessels within the vasculature of a patient.

The present invention generally provides a clot removal device for removing thrombus from a body cavity. The device has a reduced cross-sectional profile and is configured to conform to tortuosity of blood vessels. This allows the device to be advanced through blood clots and provides an enhanced flexibility for access to more tortuous lumen areas with a body vessel.

In one embodiment, the present invention provides a device for removing thrombus from a body cavity. The device comprises a flexible wire having a proximal end and a distal end extending from the proximal end. The device further comprises an elongated shaft having a proximal portion and a distal portion. The proximal portion is attached to the distal end of the flexible wire and distally extends therefrom to the distal portion. The device further comprises an expandable member formed helically about the elongated shaft. The expandable member is configured to helically close, defining a collapsed state for delivery and retrieval of the device. The expandable member is configured to helically open, defining an expanded state for removing thrombus from the body cavity. The expandable member has at least one member portion helically extending from the elongated shaft at a predetermined angle defining a proximally faced opening when the member is in the expanded state.

In another embodiment, the present invention provides a clot removal assembly for removing thrombus from a body cavity. The assembly comprises an inner catheter having a tubular body portion and an outer catheter having a distal end throughwhich the inner catheter is disposed for deployment in the body vessel. The assembly further comprises the clot removal device coaxially disposed within the inner catheter for removal of thrombus in a body cavity.

In another example, the present invention provides a method for removing thrombus from a body vessel. The method comprises percutaneously introducing an inner catheter in the body vessel. The inner catheter has a tubular body portion. The method further comprises disposing the clot removal device in a collapsed state coaxially within the inner catheter. The method further comprises deploying the device in the collapsed state into the body vessel proximal to the thrombus, and advancing the device in the collapsed state through the thrombus. The method further comprises opening the expandable member to the expanded state to receive the thrombus for removal of the thrombus from the body vessel, and retracting the device with the thrombus in the expandable member thereby removing the thrombus from the body vessel.

Further objects, features, and advantages of the present invention will become apparent from consideration of the following description and the appended claims when taken in connection with the accompanying drawings.

BRIEF DESCRIPTION OF THE DRAWINGS

FIG. 2a is a perspective view of the device of FIG. 1.

FIG. 2b is a side view of a distal portion of the device in FIG. 2a.

FIG. 2d is a cross-section end view of the device of FIG. 2c taken along line d-d.

FIG. 3a is a side view of a clot removal assembly for removing thrombus from a body cavity in accordance with one embodiment of the present invention.

FIG. 3b is an exploded view of the assembly in FIG. 3a.

DETAILED DESCRIPTION OF THE INVENTION

The present invention generally provides a clot removal device having a reduced cross-sectional profile and configured to conform to tortuosity of blood vessels, allowing for the device to be more easily advanced through blood clots and providing an enhanced flexibility for access to more tortuous lumen areas with a body vessel. The device has an elongated shaft and an expandable member formed helically about the elongated shaft. The expandable member has at least one member portion, preferably a plurality of member portions, helically extending from the elongated shaft at a predetermined angle. The member portions allow the elongated shaft to maintain its flexibility as it is advanced through a tortuous body vessel. By turning the shaft in one radial direction, the expandable member may be helically closed or helically opened. When helically closed, the device may be delivered through a blood clot in a body vessel. The device may be used to capture and retrieve the blood clot when helically opened.

Figure 1:
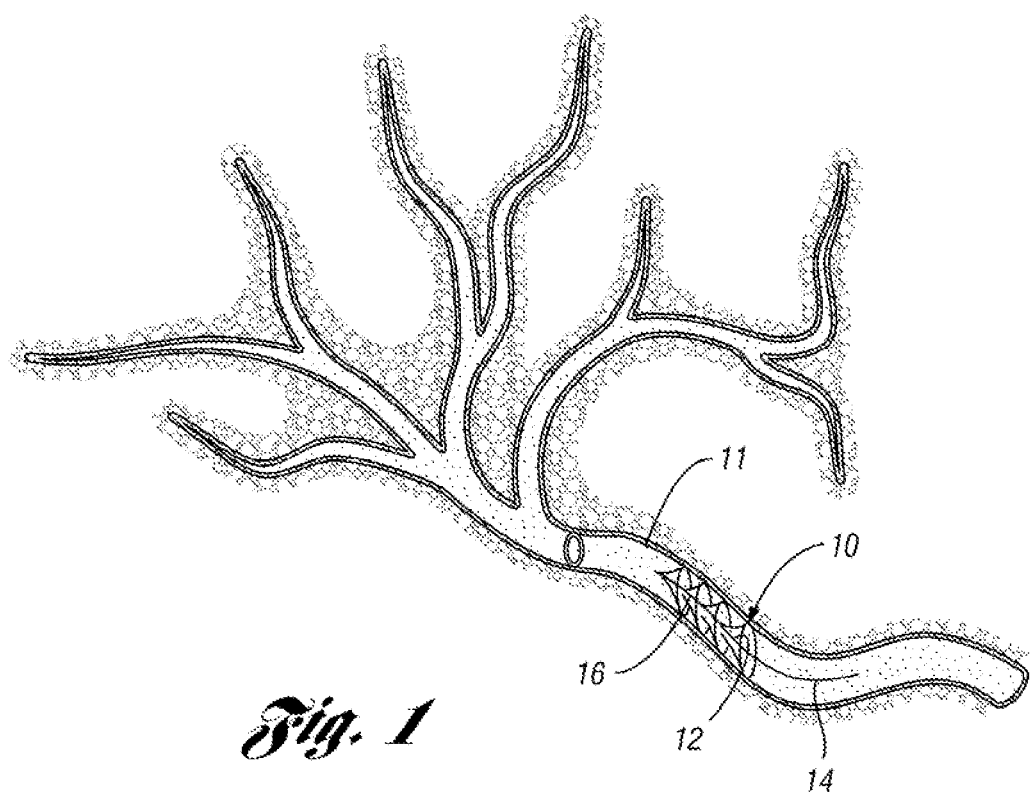
FIG. 1 is environmental view of a clot removal device for removing thrombus from a body cavity in accordance with one embodiment of the present invention.

FIG. 1 illustrates a clot removal device 10 for removing thrombus 11 from a body vessel 13 in accordance with one embodiment of the present invention. As shown, the device 10 comprises an elongated shaft 12 about which an expandable member 14 is formed. The expandable member 14 may be helically closed to define a collapsed state and helically opened to define an opened state.

FIG. 2a depicts the clot removal device 10 comprising a flexible wire 15 having a proximal end 16 and a distal end 18 extending from the proximal end 16. The flexible wire 15 is preferably a tubular member to allow for enhanced flexibility and for a wire guide to be advanced therethrough. However, the flexible wire 15 may have a center core and be used as a wire guide without falling beyond the scope or spirit of the present invention.

Figure 2C:
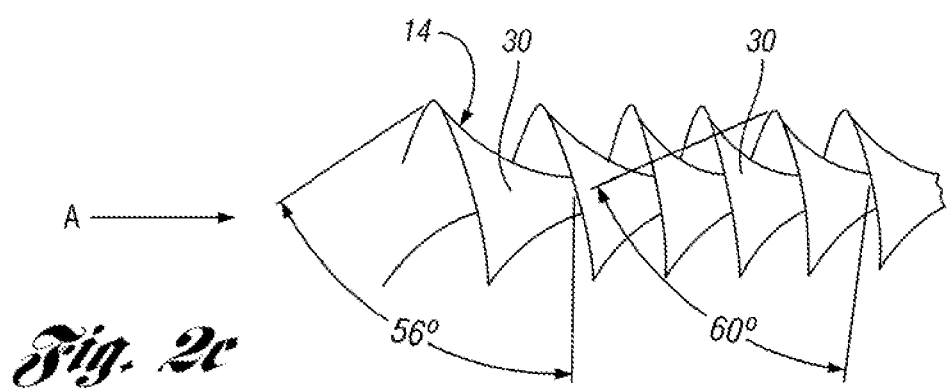
FIG. 2c is an enlarge view of the device in FIG. 2b.
Figure 2B:
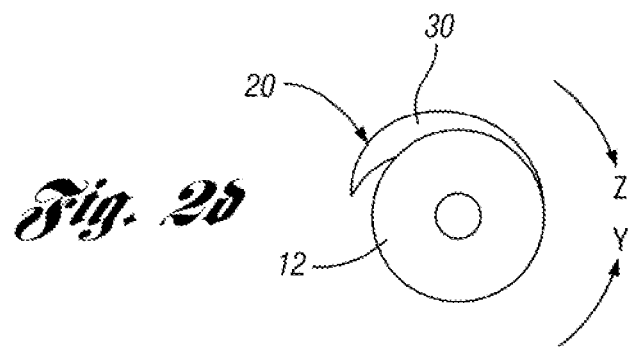

As shown in FIGS. 2a-2b, the elongated shaft 12 has a first diameter $D_1$. The elongated shaft 12 includes a proximal portion 22 and a distal portion 24 extending from the proximal portion 22. Preferably, the proximal portion 22 is attached to the distal end 18 of the flexible wire 15 and distally extending therefrom to the distal portion 24. As with the flexible wire 15, the elongated shaft 12 too is preferably a tubular member for enhanced flexibility and to allow for a wire guide to be advanced therethrough. However, the elongated shaft 12 may have a center core and may be used as a wire guide without falling beyond the scope or spirit of the present invention.

This may be accomplished by any suitable means such as by machining the expandable member 14 helically around the elongated shaft 12 disposed about a mandrel. However, any other way of forming the expandable member 14 helically about the elongated shaft 12 may be used without falling beyond the scope or spirit of the present invention.

FIGS. 2b and 2c depict the expandable member 14 formed helically about the elongated shaft 12. In this embodiment, the expandable member 14 is configured to helically close, defining a collapsed state for delivery and retrieval of the device 10. Moreover, the expandable member 14 is configured to helically open to define an expanded state for removing thrombus from the body cavity. The expandable member 14 occupies a second diameter $D_2$ that varies based on the expanded and collapsed state thereof.

As shown, the expandable member 14 comprises at least one member portion 30, preferably a plurality of member portions 30, each of which is integrally formed with another member portion 30. Each member portion 30 is helically formed and outwardly extends from the elongated shaft 12 at a predetermined angle defining a proximally faced opening when the member is in an expanded state. In one embodiment, the predetermined angle is between about 40 and 70 degrees and preferably between about 55 and 65 degrees.

As shown, each of the plurality of member portions 30 is in coaxial alignment with each other about the elongated shaft 12. Preferably, each member portion 30 is helically formed integrally with the elongated shaft 12 and extends therefrom. This allows the elongated shaft 12 to maintain its flexibility with the first diameter $D_1$ for advancement through tortuous areas within a body vessel.

FIG. 2b-2d illustrate that the expandable member 14 and the elongated shaft 12 are formed along a longitudinal axis X. The expandable member 14 may be helically closed in the collapsed state when the elongated shaft 12 or the expandable member 14 is rotated about the longitudinal axis in a first direction Y. The expandable member 14 may be helically opened in the expanded state when the elongated shaft 12 or the expandable member 14 is rotated about the longitudinal axis in a second direction Z.

As mentioned above, the device may be made of shape memory material, or may be configured to have shape memory defining the predetermined shape thereof in the deployed state. For example, the device may be comprised of any suitable material such as a pre-configured polymeric material, superelastic material, stainless steel wire, cobalt-chromium-nickel-molybdenum-iron alloy, or cobalt-chrome alloy. In one example, the device may be made of pre-configured polymeric material which takes on a predetermined shape, e.g. helical, when in the expanded state.

It is understood that the device may be formed of any other suitable material that may result in a self-opening or self-expanding device, such as shape memory materials or alloys. Shape memory alloys have the desirable property of becoming rigid, i.e., returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one example, the device is made from material including Nitinol with a transition temperature that is slightly below normal body temperature of humans, which is about 98.6° F. Thus, when the device 10 is deployed and exposed to normal body temperature, the alloy of the device will transform to austenite, that is, the remembered state, which for one embodiment of the present invention is the expanded state when deployed in the body vessel. To remove the device, the device is cooled to transform the material to martensite which is more ductile than austenite, making the device more malleable. As such, the device can be more easily collapsed and pulled into a lumen of a catheter for removal.

The thrombus removal device mentioned above may be used independently without any other delivery system or mechanism. Alternatively, the device 10 may be used, for example, with an assembly 60 as depicted in FIGS. 3a and 3b. As shown, the assembly 60 includes an inner catheter 62 having a tubular body portion and an outer catheter 63 having a distal end 64 through which the inner catheter 62 and the device is positioned for deployment in a body vessel. The inner catheter 62 is preferably made of a soft, flexible material such as silicon or another suitable material. Generally, the inner catheter 62 also has a proximal end 66 and a plastic adaptor or hub 68 to receive the thrombus removal device 10. The size of the inner catheter 62 may be based, for example, on the size of the body vessel into which the inner catheter 62 is to be inserted and a first outer diameter of the helical coil.

The assembly 60 may also include a wire guide 70 configured to be percutaneously inserted within the vasculature to guide the inner catheter 62 to a location adjacent the clot or thrombus. Alternatively, the thrombus removal device 10 may be employed as a wire guide. The device 10 is placed in the inner catheter 62 prior to treatment of the thrombus. The device is then guided through the inner catheter 62 from the hub 68 and distally beyond the distal end 64 of the inner catheter 62 to a location within the vasculature near the thrombus or clot.

The assembly 60 may include a polytetrafluoroethylene (PTFE) introducer sheath 74 for percutaneously introducing the wire guide 70 and the inner catheter 62 into a body vessel. Of course, any other suitable material may be used for the introducer sheath 74. The introducer sheath 74 may have any suitable size, for example, between about three-french and eight-french. The introducer sheath 74 facilitates inserting the inner catheter 62 percutaneously to a desired location in the body vessel and provides stability to the inner catheter 62 at the desired location in the body vessel. For example, as the introducer sheath 74 is held stationary within the body vessel it adds stability to the inner catheter 62 as the inner catheter 62 is advanced through the introducer sheath 74 to the desired location in the vasculature.

When the distal end 64 of the inner catheter 62 is at the location near the thrombus the guide wire 70 is removed, if necessary, and the thrombus removal device 10 is inserted into the inner catheter 62 and is advanced coaxially through the inner catheter 62 for deployment through the distal end 64 of the inner catheter 62. In this configuration, a proximal end of the shaft can be used to mechanically advance or push the thrombus removal device 10 through the inner catheter 62.

Figure 4:
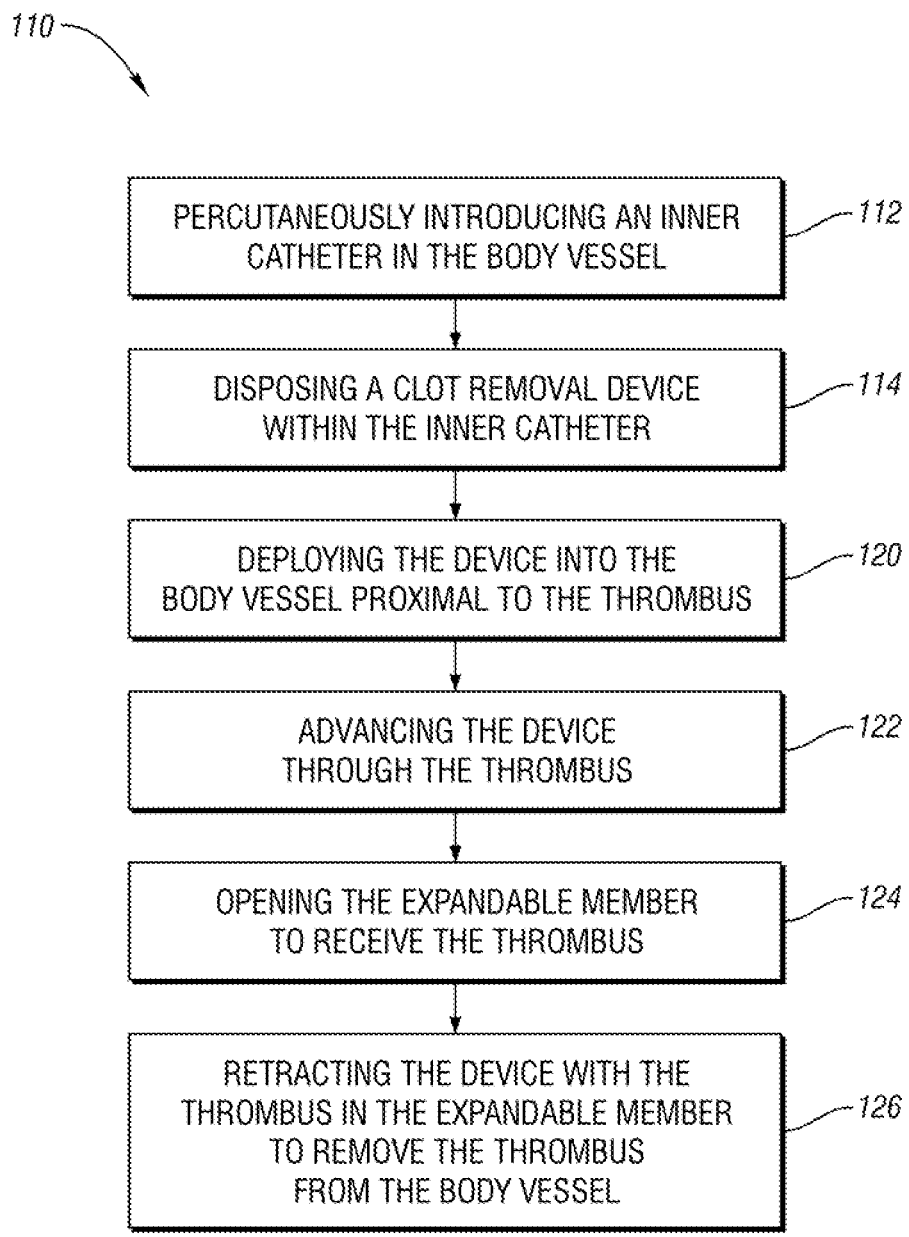
FIG. 4 is a flowchart of a method for removing thrombus from a body vessel in accordance with one example of the present invention.

Turning now to FIG. 4, there is shown one example of a sequence of steps of a method 110 for removing thrombus from a body vessel when employing the assembly 60 and the thrombus removal device 10 in accordance with one example of the present invention. In step 112, the method 110 includes a physician percutaneously introducing the inner catheter 62 into the body vessel. The physician may use any suitable means, for example, fluoroscopy, to verify the placement of inner catheter 62.

In step 114, the thrombus removal device 10 is disposed into the inner catheter 62 in a closed state. The method further comprises deploying the removal device in step 120 in the collapsed state into the body vessel proximal to the thrombus. As mentioned above, the expandable member is helically closed in the collapsed state when the elongated shaft is rotated about the longitudinal axis in a first direction and the expandable member is helically opened in the expanded state when the elongated shaft is rotated about the longitudinal axis in a second direction.

The method further comprises advancing the device in step 122 in the collapsed state through the thrombus. In step 124, the method further comprises opening the expandable member to the expanded state to receive the thrombus for removal of the thrombus from the body vessel. As mentioned above, this may be accomplished by rotating the elongated shaft about the longitudinal axis in the second direction.

In step 126, the method further comprises retracting the device with the thrombus in the expandable member thereby removing the thrombus from the body vessel. As mentioned above, this may be accomplished by rotating the elongated shaft about the longitudinal axis in the first direction to secure the thrombus in the expandable member. After capturing the thrombus, the physician may advance the device further in the distal direction toward additional thrombi that may reside in the vessel and then repeat the above procedure to capture the additional thrombi.

Figure 5:
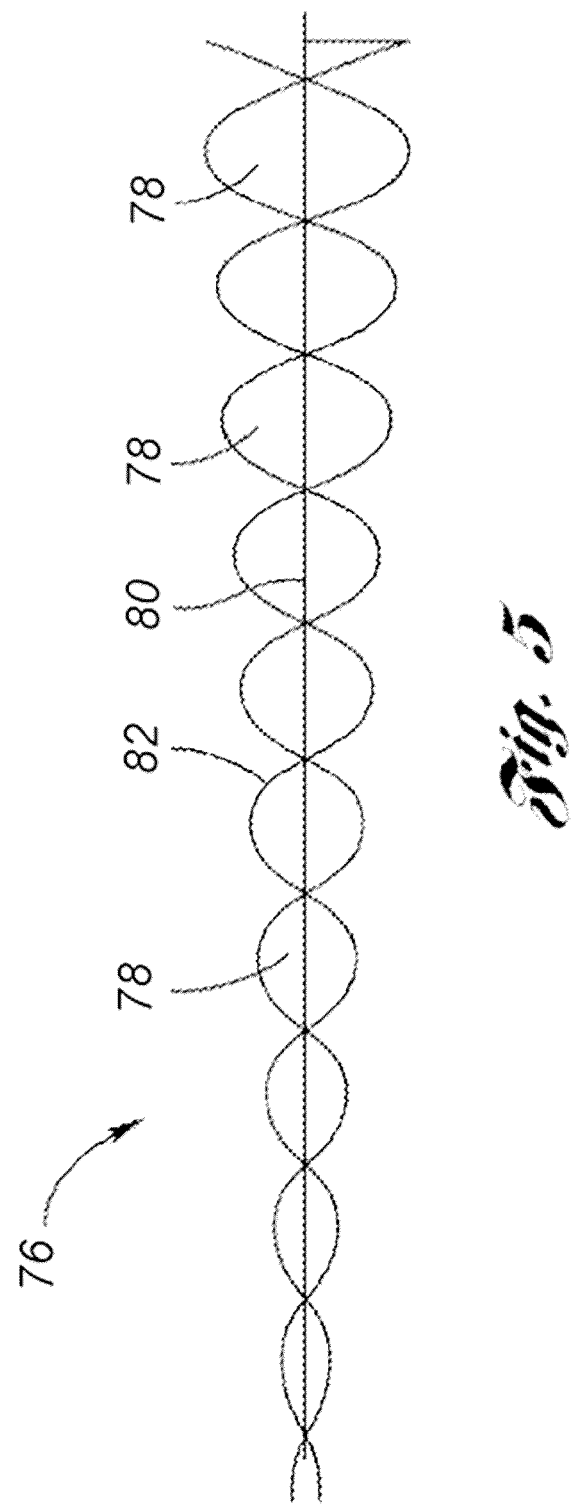
FIG. 5 is side view of a clot removal device for removing thrombus from a body cavity in accordance with an embodiment of the present invention.

FIG. 5 illustrates a clot removal device 76 having a varying second or outer diameter $D_2$ in accordance with another embodiment of the present invention. The device 76 has similar components as the device 10 mentioned above, except that in this embodiment, each member portion 78 includes a proximally faced opening having an outer diameter $D_2$ that increases distally. That is, the outer diameter $D_2$ increases distally longitudinally relative to the elongated shaft 80 to define the expandable member 82 having a distally flared profile.

While the present invention has been described in terms of preferred embodiments, it will be understood, of course, that the invention is not limited thereto since modifications may be made to those skilled in the art, particularly in light of the foregoing teachings.

The invention claimed is:

1. A device for removing a thrombus from a body cavity, the device comprising:
   a flexible wire having a proximal end and a distal end;
   an elongated shaft having a proximal portion and a distal portion, the proximal portion attached to the distal end of the flexible wire and distally extending therefrom to the distal portion; and
   an expandable member formed helically about the elongated shaft, the expandable member being configured to helically close defining a collapsed state for delivery and retrieval of the device, the expandable member being configured to helically open defining an expanded state for removing a thrombus from the body cavity, the expandable member having a plurality of member portions helically opening and extending from the elongated shaft, each of the member portions helically extending proximally at a predetermined angle relative to the elongated shaft and defining a helical proximally faced opening when the member portion is in the expanded state, the expandable member is disposed along a longitudinal axis, the expandable member being helically closed in the collapsed state when the elongated shaft is rotated about the longitudinal axis in a first direction, wherein adjacent member portions overlap each other.

2. The device of claim 1 wherein the predetermined angle is between about 40 and 70 degrees.

3. The device of claim 1 wherein the predetermined angle is between about 55 and 65 degrees.

4. The device of claim 1 wherein each of the plurality of member portions is in coaxial alignment with each other about the elongated shaft.

5. The device of claim 1 wherein the expandable member is helically opened in the expanded state when the elongated shaft is rotated about the longitudinal axis in a second direction.

6. The device of claim 1 wherein the expandable member comprises at least one of the following materials: superelastic material, nitinol, polymeric material.

7. The device of claim 1 wherein the opening of each member portion has an outer diameter, the outer diameter increasing distally longitudinally relative to the elongated shaft to define the expandable member having a distally flared profile.

8. The device of claim 1 wherein the member portions are integral with each other.

9. A clot removal assembly for removing a thrombus from a body cavity, the assembly comprising:
   an inner catheter having a tubular body portion;
   an outer catheter having a distal end through which the inner catheter is disposed for deployment in the body vessel; and
   a clot removal device coaxially disposed within the inner catheter for removal of thrombus in a body cavity, the device comprising:
      a flexible wire having a proximal end and a distal end;
      an elongated shaft having a proximal portion and a distal portion, the proximal portion attached to the distal end of the flexible wire and distally extending therefrom; and
      an expandable member formed helically about the distal portion of the elongated shaft, the expandable member being configured to helically close defining a collapsed state for delivery and retrieval of the device, the expandable member being configured to helically open defining an expanded state for removing a thrombus from the body cavity, the expandable member having a plurality of member portions helically opening and extending from the elongated shaft, each of the member portions helically extending proximally at a predetermined angle relative to the elongated shaft and defining a helical proximally faced opening when the member portion is in the expanded state, the expandable member is disposed along a longitudinal axis, the expandable member being helically closed in the collapsed state when the elongated shaft is rotated about the longitudinal axis in a first direction, wherein adjacent member portions overlap each other.

10. The assembly of claim 9 further comprising:
   an introducer sheath through which the outer catheter is inserted for percutaneous insertion to the body vessel; and
   a wire guide introducible through the introducer sheath to the body cavity for guidance of the inner and outer catheters to the body cavity.

11. The assembly of claim 9 wherein the predetermined angle is between about 40 and 70 degrees.

12. The assembly of claim 9 wherein the predetermined angle is between about 55 and 65 degrees.

13. The assembly of claim 9 wherein the opening of each member portion has an outer diameter, the outer diameter increasing distally longitudinally relative to the elongated shaft to define the expandable member having a distally flared profile.

14. The assembly of claim 9 wherein the expandable member is helically opened in the expanded state when the elongated shaft is rotated about the longitudinal axis in a second direction.

15. A device for removing a thrombus from a body cavity, the device comprising:
   a flexible wire having a proximal end and a distal end;
   an elongated shaft having a proximal portion and a distal portion, the proximal portion attached to the distal end of the flexible wire and distally extending therefrom to the distal portion; and
   an expandable member formed helically about the elongated shaft, the expandable member being configured to helically close defining a collapsed state for delivery and retrieval of the device, the expandable member being configured to helically open defining an expanded state for removing a thrombus from the body cavity, the expandable member having a plurality of member portions helically opening and extending from the elongated shaft, each of the member portions helically extending proximally at a predetermined angle relative to the elongated shaft and defining a helical proximally faced opening when the member portion is in the expanded state, the expandable member is disposed along a longitudinal axis, the expandable member being helically closed in the collapsed state when the elongated shaft is rotated about the longitudinal axis in a first direction, the opening of each member portion has an outer diameter, the outer diameter increasing distally longitudinally relative to the elongated shaft to define the expandable member having a distally flared profile.

16. The device of claim 15 wherein the predetermined angle is between about 40 and 70 degrees.

17. The device of claim 15 wherein the predetermined angle is between about 55 and 65 degrees.

18. The device of claim 15 wherein each of the plurality of member portions is in coaxial alignment with each other about the elongated shaft.

19. The device of claim 15 wherein the expandable member is helically opened in the expanded state when the elongated shaft is rotated about the longitudinal axis in a second direction.

20. The device of claim 15 wherein the member portions are integral with each other.

* * * * *

UNITED STATES PATENT AND TRADEMARK OFFICE
CERTIFICATE OF CORRECTION

| | | |
|---|---|---|
| PATENT NO. | : 8,419,748 B2 | Page 1 of 1 |
| APPLICATION NO. | : 11/855605 | |
| DATED | : April 16, 2013 | |
| INVENTOR(S) | : Valaie | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 782 days.

Signed and Sealed this
Thirtieth Day of December, 2014

Michelle K. Lee
*Deputy Director of the United States Patent and Trademark Office*